United States Patent [19]

Manuel

[11] 4,189,839

[45] Feb. 26, 1980

[54] UNIVERSAL ORTHODONTIC PLIERS

[76] Inventor: John L. Manuel, 960 Alexander Dr., Haysville, Kans. 67060

[21] Appl. No.: 902,559

[22] Filed: May 3, 1978

[51] Int. Cl.² .............................................. A61C 7/00
[52] U.S. Cl. ...................................................... 433/4
[58] Field of Search .................................. 32/66, 14 A

[56] References Cited

U.S. PATENT DOCUMENTS

| | | | |
|---|---|---|---|
| 1,299,103 | 4/1919 | Angle | 32/66 |
| 1,594,143 | 7/1926 | Angle et al. | 32/66 |
| 2,985,962 | 5/1961 | Shiner | 32/66 |

FOREIGN PATENT DOCUMENTS 119234  4/1930  Fed. Rep. of Germany .............. 32/66

*Primary Examiner*—Russell R. Kinsey
*Assistant Examiner*—John J. Wilson
*Attorney, Agent, or Firm*—Edward L. Brown, Jr.

[57] ABSTRACT

A pliers having a pair of jaw members each of which includes a pair of positioning legs for placing, removing and crimping light wire pins and other light wire devices. The jaws include a pair of transverse mating grooves, one in each jaw member adjacent the positioning legs and a longitudinal slot completely through the upper jaw member and partially through the lower jaw member, and a trough adjacent the partial slot in the lower jaw member for loosely receiving the spring coils of various light wire devices while the legs of the devices pass through the mating grooves of the jaw members.

12 Claims, 9 Drawing Figures

UNIVERSAL ORTHODONTIC PLIERS

BACKGROUND OF THE INVENTION

1. Field of the Invention

This invention relates to the dental art found in general Class 32 (dentistry), and more specifically to a universal pliers used in orthodontic dentistry. One of the functions of orthodontics is to correct the irregular arrangement of teeth in the dental arch. This technique involves mounting of metal bands with brackets on each tooth. Corrective forces are then applied to selected teeth through the use of wires, springs and other tensioning devices.

2. Description of the Prior Art

The patent to Angle et al, U.S. Pat. No. 1,594,143, teaches a three-legged jaw arrangement which is substantially different from the present invention's four-legged arrangement. The pair of positioning legs of the present invention hold and align light wire pins during insertion into the bracket tube. The present invention has substantially more utility than the above mentioned patent in handling light wire pins. It is also pointed out that the above mentioned Angle structure cannot hold spring devices and other auxiliaries without tightly bearing down on the device.

Another patent of interest to Angle, U.S. Pat. No. 1,299,103, teaches a pair of jaw members having pairs of legs on each jaw member. However, the longitudinal slot between the legs is so great that the various functions of the present device obviously cannot be done. It is also pointed out that there is not partial slot in either of the jaw members of this patent to provide the necessary backing for driving a pin into a bracket tube.

SUMMARY OF THE INVENTION

The various functions of the present invention have previously required a multiplicity of tools for the various functions, which the present invention accomplishes with a single tool. The positioning, removal and crimping of light wire pins can be very accurately done with the present pliers with the pair of positioning legs on the lower jaw holding the pin in alignment while the positioning legs on the upper jaw maintain alignment with the bracket tube as the pin is driven into the tube and through the longitudinal slot in the upper jaw member. By slightly rotating the upper jaw member with the pin therebetween, the pin is readily crimped into a locked position. To remove bent or stuck pins, the pliers are turned upside-down so that the slotted jaw is straddling the head of the pin with the other jaw member slightly misaligned so that one of the positioning legs is directly over the crimped end of the pin. That positioning leg is then utilized to drive the stuck pin out of the bracket tube between the slotted lower jaw member. The pliers can also remove pins by turning the pliers sideways so as to reach around the bracket tube with the jaws and tightly grasp the pin between a pair of positioning legs without damage to the bracket.

The pliers of the present invention are capable of locking onto spring devices and other auxiliaries, while allowing the device to freely move within the jaw slots without fear of damaging the coils of the spring or its legs. This eliminates the common danger of springs flying loose into the patient's mouth with the possibility of inhalation into the lungs. All prior art tools which handle springs of this nature clamp tightly on the wires or coils of the springs and quite often damage or distort the springs sufficiently so that they are no longer usable.

Therefore it is the principal object of the present invention to provide a universal pliers with a plurality of functions for use in orthodontic as well as general dental practice.

Another object of the present invention is to provide a universal pliers for handling light wire pins, arch wires, uprighting springs, torquing devices, ligature wires, separating springs, standard elastics and various other orthodontic devices.

A further object of the present invention is to provide a pliers to loosely hold separating springs and other devices so that the spring has a certain freedom of movement while still maintaining a positive hold on the spring.

Other objects and advantages of the present invention will be apparent from the following detailed description, appended claims and accompanying drawings.

DESCRIPTION OF THE PREFERRED EMBODIMENT

Figure 1:
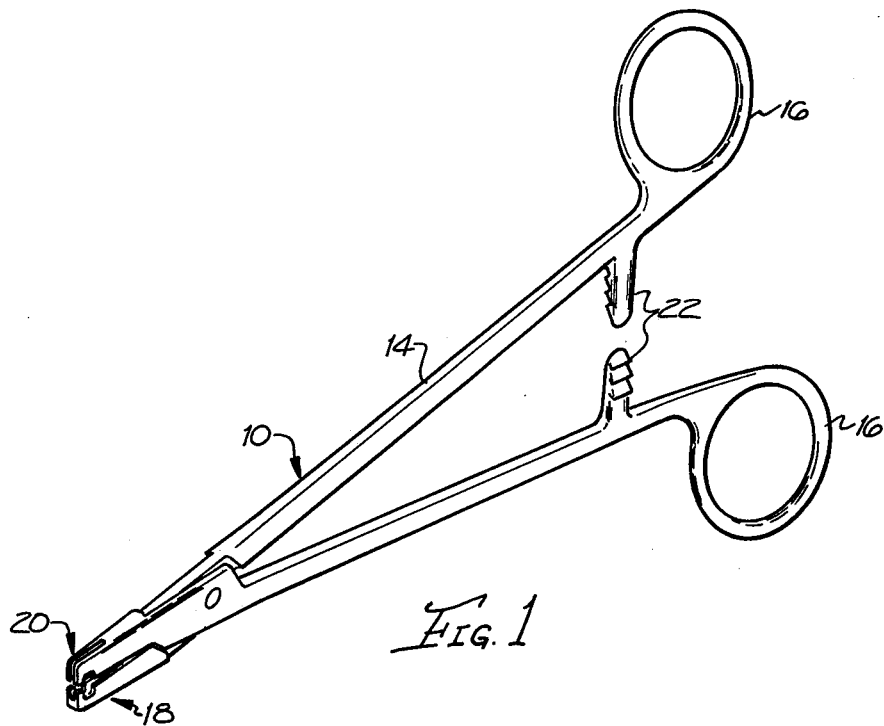
FIG. 1 is a perspective view of the orthodontic pliers of the present invention.
Figure 2:
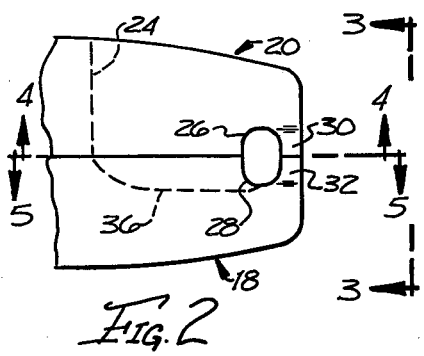
FIG. 2 is a partial side elevational view of the pliers' jaws to an enlarged scale.
Figure 3:
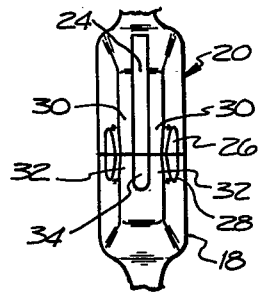
FIG. 3 is a partial end elevational view of the jaws looking in the direction of the arrows 3—3 of FIG. 2.
Figure 4:
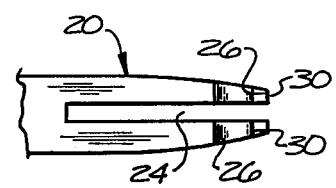
FIG. 4 is a partial view of the upper jaw taken along line 4—4 of FIG. 2.
Figure 5:
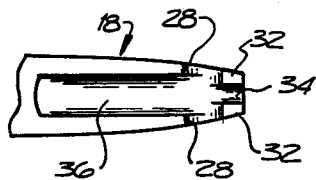
FIG. 5 is a partial view of the lower jaw taken along line 5—5 of FIG. 2.

Referring now to the drawing, FIG. 1 shows a pliers-type tool generally described by reference numeral 10 for manipulating and positioning light wire pins and other light wire auxiliaries. The pliers 10 includes a pair of lever arms 12 and 14 pivoted together with handle means 16 at one end and a pair of jaws 18 and 20 at the opposite end. Adjacent the handle means 16 are a pair of conventional locking members 22 which will releasably hold the pliers in locking position, if so desired. The upper jaw 20 of the pliers, as best seen in FIGS. 2, 3 and 4, includes a longitudinal slot 24 from the outer end of the jaw member inward. Located approximate the end of jaw 20 is a transverse mating groove 26 which mates with a similar groove 28 in a lower jaw member 18 which can be slightly deeper than groove 26. Transverse groove 26 defines in the outer end of the jaw 20, a pair of positioning legs 30 which are opposed to a similar set of positioning legs 32 on the lower jaw member 18, as seen in FIG. 3. Positioning legs 32, as seen in FIG. 5, are separated by a partial longitudinal slot 34 which is oppositely positioned and in alignment with longitudinal slot 24 in upper jaw member 20, as seen in FIG. 3. Located in lower jaw member 18 is a spring trough 36 which extends inwardly on the jaw from transverse groove 28.

HANDLING OF LIGHT WIRE PINS

Figure 7:
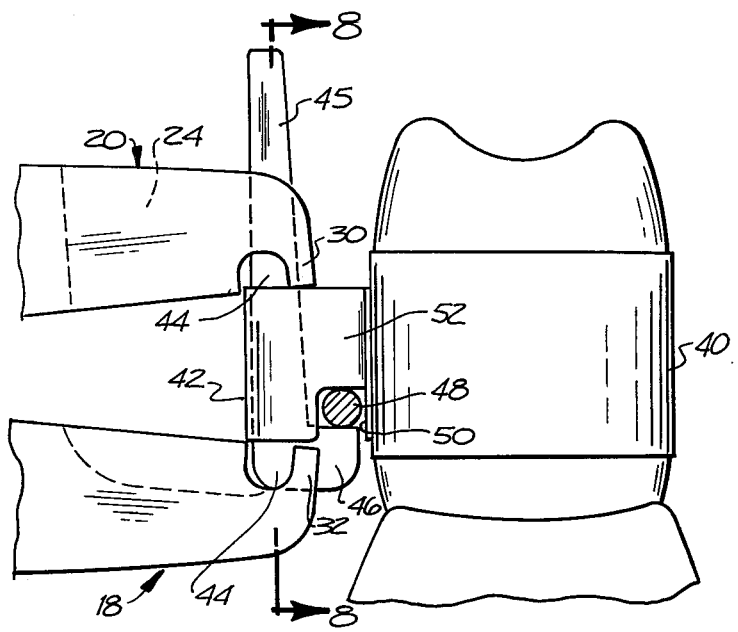
FIG. 7 is a side elevational view of the pliers' jaws inserting a light wire pin in a bracket tube.
Figure 8:
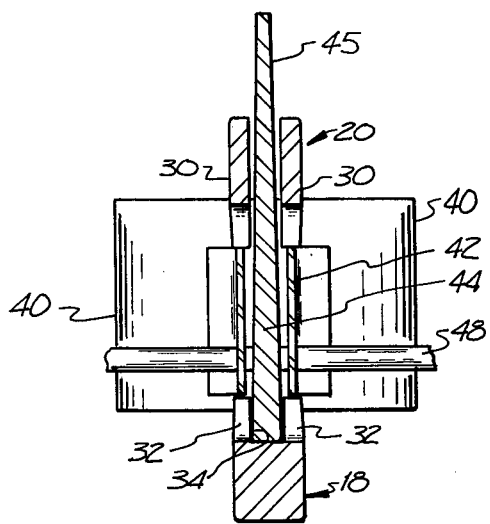
FIG. 8 is a sectional view taken along line 8—8 of FIG. 7.

In light wire orthodontics, various teeth in the patient's mouth are surrounded by a bracket band 40, as illustrated in FIG. 7. Attached to the front side of band 40 is a bracket tube 42 which receives pin 44, having an offset head portion 46 which in turn holds an arch wire 48 within the slot 50 on the bracket. Various shaped pins are used depending upon the desired position of the arch wire relative to the bracket tube 42. The pins, which are very small, can be picked up by the pliers in two different ways, the first being direct clamping of the pin head between a pair of opposing legs 30 and 32. The second method involves depositing some wax in the partial slot 34 of the lower jaw member so as to hold the pin head 46 in place once inserted in the lower jaw member, which can be seen in FIG. 8. Pin 44 snugly fits in slot 34 so that the pin's alignment is maintained with jaw 20 of the pliers, with the jaws wide open. By closing the jaws, the tail end 45 of the pin 44 is forced up through the bottom end of bracket tube 42 between the legs 30 of the upper jaw 20. The positioning legs 30 on the upper jaw not only lever against the top surface of the bracket tube 42, but also maintain the upper jaw 20 in alignment for receipt of the tail end 45 of the pin. As the jaws are brought together, the pin slides upward in the bracket tube 42, lifting arch wire 48 into the proper position in bracket slot 50. Once pin 44 is in its proper position, the tail 45 of the pin is bent to one side locking the pin in its proper position. This is achieved by merely lightening the pressure on the lower jaw and rotating the upper jaw so as to crimp the pin in place before cutting off the excess end. If it is desired to fully crimp the tail 45, the upper jaw 18 is rotated a full 90° to the right or left from its position seen in FIG. 8.

Figure 9:
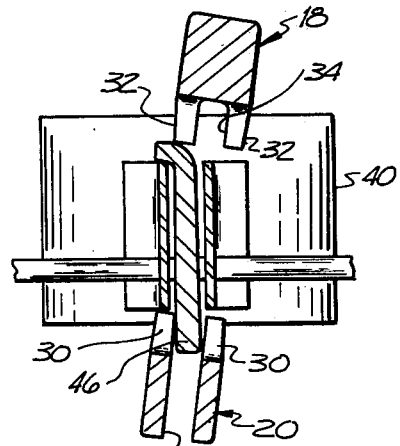
FIG. 9 is a similar sectional view to FIG. 8 with the pliers turned upside-down for a removal function.

To remove a crimped or bent pin, the pliers 10 are turned upside-down, as seen in FIG. 9, so that the lower jaw having the partial slot 34 is positioned adjacent the tail end of the pin 45 while the upper jaw 20 straddles the head end 46 of the pin. Lower jaw 18 is cocked slightly off to one side, as seen in FIG. 9, so that the left positioning leg 32 is directly over the pin; so that it performs a punching action when the jaws are brought together forcing the bent pin 44 downwardly through the longitudinal slot 24 in the upper jaw 20.

POSITIONING OF SEPARATING SPRINGS AND OTHER AUXILIARIES

Figure 6:
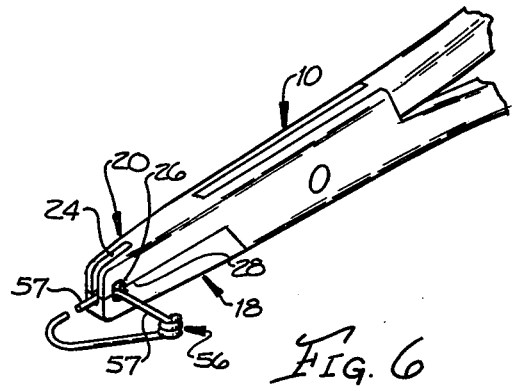
FIG. 6 is a perspective view of the pliers' jaws engaging an orthodontic device.

FIG. 6 illustrates a separating spring 56 loosely held by the pliers 10 with the gingival leg 57 of the spring passing through the pair of mating grooves 26 and 28 and then out the front of the jaws through longitudinal slot 24. The leg 57 of the spring device is free to move in slot 24 through approximately 120° of angular movement. This freedom of movement allows sufficient latitude to the orthodontist to guide the leg 57 of the spring into an engaging position between the teeth while still preventing the spring device from being separated from the pliers until the orthodontist opens the jaws. This novel function is not only much safer than the prior art method of tightly locking the plier jaws on the spring wire, but also insures that the spring device will not be damaged.

While not illustrated in the drawings, other types of coil spring devices can be held by the pliers with the coil springs positioned in the spring trough 36 while the legs of the spring extend outwardly through longitudinal slot 24 and mating grooves 26 and 28. The four positioning legs 30 and 32 of the pliers allow a plurality of other holding positions on various auxiliaries specifically mentioned.

While particular embodiments of this invention have been shown and described, it is to be understood that modifications may be made within the scope of the accompanying claims and protection is sought to the broadest extent the prior art allows.

What is claimed is:
1. A universal orthodontic pliers comprising:
   a pair of lever arms pivoted together having handle means at one end and jaw means at the opposite end;
   the jaw means including an upper and a lower jaw member;
   a pair of transverse mating grooves, one in each jaw member;
   a pair of positioning legs on the end of each jaw member oppositely positioned from each other;
   a longitudinal slot passing through the upper jaw member between said pair of positioning legs;
   a partial longitudinal slot in the lower jaw member oppositely positioned from the slot in the upper jaw member with the pair of positioning legs defining the sides of the partial slot, both slots being of a width less than the width of the transverse grooves.
2. A universal orthodontic pliers as set forth in claim 1, including a trough means in the lower jaw member for loosely receiving spring coils, the trough means extending longitudinally inward on the jaw member from the partial slot and has a width substantially greater than the partial slot.
3. A universal orthodontic pliers as set forth in claim 1, wherein said transverse groove in each jaw member has a depth greater than half the width of the groove so that when the grooves are in mating contact, the opening defined has a width less than the combined depth of both transverse grooves.
4. A universal orthodontic pliers as set forth in claim 1, wherein the longitudinal slot in the upper jaw member and partial slot in the lower jaw member are defined by the space between each pair of positioning legs and each slot is of a width substantially the same as each positioning leg.
5. A universal orthodontic pliers as set forth in claim 1, wherein the depth of the transverse groove in the lower jaw member is greater than that in the upper jaw member.
6. A universal orthodontic pliers as set forth in claim 1, wherein each jaw member has a plane of contact with its opposing jaw member; lying in said planes are the ends of the positioning legs of each jaw member and the edges of said transverse grooves.
7. A universal orthodontic pliers comprising:
   a pair of lever arms pivoted together with handle means at one end and jaw means at the other;
   the jaw means includes an upper and a lower jaw member each having a contacting surface;
   a pair of transverse mating grooves, one in the contacting surface of each jaw member;
   a pair of parallel positioning legs on the ends of each jaw member, oppositely aligned with the opposing jaw member, with the ends of said legs in the contacting surface;
   a longitudinal slot passing through the upper jaw member between said pair of positioning legs; and
   a partial longitudinal slot in the lower jaw member oppositely positioned and aligned with the slot in the upper jaw member with the pair of positioning legs defining the sides of the partial slot, both slots being of width less than the transverse grooves.

8. A universal orthodontic pliers as set forth in claim 7, including a trough means in the contacting surface of the lower jaw member for loosely receiving spring coils, the trough means extends longitudinally inward on the jaw member from the partial slot and has a width substantially greater than the partial slot.

9. A universal orthodontic pliers as set forth in claim 7, wherein said transverse groove in each jaw member has a depth greater than half the width of the groove so that when the grooves are in mating contact, the opening defined has a width less than the combined depth of both transverse grooves.

10. A universal orthodontic pliers as set forth in claim 7, wherein said transverse groove in each jaw member has a depth greater than half the width of the groove so that when the grooves are in mating contact, the opening defined has a width less than the combined depth of both transverse grooves and the groove in the lower jaw member is greater than that in the upper jaw member.

11. A universal orthodontic pliers as set forth in claim 7, wherein the longitudinal slot in the upper jaw member and partial slot in the lower jaw member are defined by the space between each pair of positioning legs and each slot is of a width substantially the same as each positioning leg.

12. A universal orthodontic pliers as set forth in claim 7, wherein the positioning legs are tapered toward their free ends.

* * * * *